(12) United States Patent
Bauer et al.

(10) Patent No.: US 12,241,850 B2
(45) Date of Patent: Mar. 4, 2025

(54) FOOD PROCESSING MONITORING SYSTEM

(71) Applicant: HOLLYMATIC CORPORATION, Countryside, IL (US)

(72) Inventors: Erik Bauer, Alto, MI (US); Victor Guynn, Romeoville, IL (US)

(73) Assignee: HOLLYMATIC CORPORATION, Countryside, IL (US)

( * ) Notice: Subject to any disclaimer, the term of this patent is extended or adjusted under 35 U.S.C. 154(b) by 712 days.

(21) Appl. No.: 17/313,470

(22) Filed: May 6, 2021

(65) Prior Publication Data
US 2022/0357293 A1   Nov. 10, 2022

(51) Int. Cl.
| | | |
|---|---|---|
| *G01N 25/00* | (2006.01) | |
| *A22C 5/00* | (2006.01) | |
| *A22C 17/00* | (2006.01) | |
| *B01F 27/70* | (2022.01) | |
| *B01F 35/21* | (2022.01) | |

(Continued)

(52) U.S. Cl.
CPC ......... *G01N 25/00* (2013.01); *A22C 17/0026* (2013.01); *B01F 35/2115* (2022.01); *B01F 35/212* (2022.01); *G01K 3/005* (2013.01); *A22C 5/00* (2013.01); *A22C 17/00* (2013.01); *B01F 27/70* (2022.01); *B01F 2101/06* (2022.01); *G01K 13/00* (2013.01); *G01K 2207/04* (2013.01); *G01K 2207/06* (2013.01); *G01N 25/005* (2013.01); *G01N 33/12* (2013.01)

(58) Field of Classification Search
CPC ...... G01N 25/00; G01N 25/005; G01N 33/12; A22C 17/0026; A22C 17/00; A22C 5/00; B01F 35/2115; B01F 35/212; B01F 27/70; B01F 2101/06; G01K 2207/04; G01K 2207/06; G01K 13/00; G01K 1/026; G01K 3/005
See application file for complete search history.

(56) References Cited

U.S. PATENT DOCUMENTS 7,308,322 B1 * 12/2007 Discenzo ........... G05B 23/0221
                                                      702/182
10,065,196 B1   9/2018 Tran et al.
(Continued)

FOREIGN PATENT DOCUMENTS

| CN | 108497952 A | 9/2018 |
|---|---|---|
| CN | 109965739 A | 7/2019 |

(Continued)

*Primary Examiner* — Lisa M Caputo
*Assistant Examiner* — Christian T Bryant
(74) *Attorney, Agent, or Firm* — Sughrue Mion, PLLC

(57) ABSTRACT

Food processing monitoring systems and method thereof are provided. A method includes obtaining first temperature data from a first temperature sensor at an inlet of a food processing machine; obtaining second temperature data from a second temperature sensor at an outlet of the food processing machine; obtaining current data from a current sensor that is configured to measure current of a motor of the food processing machine; determining presence of food product at the inlet based on a peak current, of the current data at a time the motor starts, being greater than a first current threshold; and logging a temperature of the first temperature data based on the peak current being greater than the first current threshold.

18 Claims, 5 Drawing Sheets

(51) Int. Cl.
  *B01F 35/212* (2022.01)
  *G01K 3/00* (2006.01)
  *G01K 13/00* (2021.01)
  *G01N 33/12* (2006.01)
  *B01F 101/06* (2022.01)

(56) References Cited

U.S. PATENT DOCUMENTS

| | | | |
|---|---|---|---|
| 2005/0188859 A1* | 9/2005 | Bruce, III | G01N 21/359 |
| | | | 99/486 |
| 2006/0044935 A1* | 3/2006 | Benelli | A47J 43/044 |
| | | | 366/206 |
| 2009/0080607 A1* | 3/2009 | Hoffmann | A22C 11/0245 |
| | | | 378/53 |
| 2016/0214115 A1 | 7/2016 | Bauer et al. | |
| 2016/0256001 A1 | 9/2016 | Lehotay et al. | |

FOREIGN PATENT DOCUMENTS

| | | | | |
|---|---|---|---|---|
| CN | 110665613 A | 1/2020 | | |
| DE | 102005032678 A1 * | 1/2007 | | A22C 11/08 |
| JP | 2004-321840 A | 11/2004 | | |

* cited by examiner

| Mode | Duration | Peak Motor Current | Average Motor Current | Product Present | Product Temperature (Hopper) | Product Temperature (Outlet) | Ambient Temperature |
|---|---|---|---|---|---|---|---|
| Startup | x | x | | x | x | | x |
| Operation without product | x | x | x | | | | x |
| Grinding | x | x | x | x | x | x | x |
| Grinding complete | x | x | x | | | | x |

FOOD PROCESSING MONITORING SYSTEM

BACKGROUND

Technical Field

Examples embodiments of the present disclosure relate to a system for monitoring a food processing system (e.g. a mixer grinder) for preparing a product such as ground meat.

Description of Related Art

Mixer grinder apparatuses may be used in the food processing industry.

As one example of an applicable mixer grinder, see U.S. Pat. No. 3,548,903 A to Holly, issued Dec. 22, 1970, which is hereby incorporated by reference in its entirety. An applicable mixer grinder machine processes a product, which may include meat, vegetables, fruits, cheese, and sauces, for example. Another mixer grinder is described in U.S. Patent Publication No. 2016/0214115 A1 to Bauer et al., published Jul. 28, 2016, which is hereby incorporated by reference in its entirety.

In a conventional mixer grinder, such as that described in Holly, mixing is achieved by folding or tumbling the product in a hopper by a set of rotating mixing blades. One example of the product is coarsely cut meat. The mixed meat is then passed directly to a grinder. In the bottom of the hopper, there is located an exit opening through which the mixed meat passes. Positioned beneath the opening from the hopper there is a meat receiving grinding chamber where a meat moving feed screw leading to a conventional grinding head is located.

In operation, mixing action by the rotating mixing blades and paddles urges the meat back and forth in the hopper, which tumbles and folds the meat so that very thorough mixing is accomplished. Then, when mixing is sufficiently complete, grinding is commenced by initiating driving of the feed screw. The feed screw, which has a large pitch adjacent the exit opening and a progressively smaller pitch toward the grinding head, rapidly forces the mixed meat through the grinding head. The output is ground meat.

If a second (e.g., finer) grinding is desired, this ground meat is then returned to the hopper and processed again. In this instance, mixing can be continued simultaneously with the grinding if desired. Alternatively, two of the above described mixer grinders can be connected in series such that the outlet from the grinding head of the first mixer grinder is fed directly into the hopper of the second mixer grinder. An example of such a system is the "Gemini System" produced and sold by Hollymatic Corporation.

SUMMARY

Food safety in food processing equipment is of critical importance to prevent customers from contracting foodborne illnesses. Accordingly, there is a need to improve monitoring in food processing equipment to increase food safety.

One way of ensuring food safety in meat processing equipment is to monitor the temperature of the food product to ensure it does not rise above the temperature at which bacteria may grow. Within food processing equipment, this may be done using temperature sensors attached to the equipment to monitor the temperature of the product as it is being processed. In addition, this temperature data may be logged electronically either on a local storage media or on a remote data collection system. One challenge with this data collection system however is that, if food safety is measured by inlet and outlet temperature in a remotely monitored food processing equipment such as a grinder, a static temperature threshold may not be reliable for determining food safety. This is due to the fact that the ambient room temperature may be above the threshold for food safety which can cause false alarms for food temperature measurement. For example, if a meat grinder is operating in a room at 50° F. and meat product with a starting temperature of 33° F. is placed in the grinder, the temperature readings at the outlet of the grinder will remain at 50° F. until the meat has started to extrude from the outlet of the grinder. If a temperature limit of 40° F. is used to alert an operator or a data collection system of an unsafe temperature condition, this may result in a false alarm whenever the equipment does not have food product present (either at the start of an operation cycle before food has been loaded or at the end once all of the product has been processed).

An additional sensor such as a light curtain, weight sensors, or other presence detection sensors may provide the system with information regarding whether food product is actually present in the machine. However, optical sensors can become dirty and unreliable when used in such environments, and a weight sensor may not be able to detect product in a rotating hopper with a heavy piece of equipment.

Example embodiments of the present disclosure may overcome the above problems and/or other problems.

According to one or more embodiments, a food processing monitoring system is provided. The food processing monitoring system includes a food processing machine that includes: an inlet configured to receive food product; an outlet configured to receive the food product after being processed; a processing chamber that is connected to the inlet and the outlet; a rotatable shaft that is within the processing chamber; and a motor that is configured to rotate the rotatable shaft such as to cause the food product to be processed in the processing chamber. The food processing monitoring system further includes: a first temperature sensor provided at the inlet; a second temperature sensor provided at the outlet; a current sensor configured to measure current of the motor; and a computer system that includes memory and at least one processor. The computer system is configured to: obtain first temperature data from the first temperature sensor; obtain second temperature data from the second temperature sensor; obtain current data from the current sensor; determine presence of the food product at the inlet based on a peak current, of the current data at a time the motor starts, being greater than a first current threshold; and log a temperature of the first temperature data based on the peak current being greater than the first current threshold.

According to an embodiment, the temperature of the first temperature data is logged as a temperature of the food product at the inlet.

According to an embodiment, the computer system is further configured to log a temperature of the second temperature data based on a predetermined time delay after the presence of the food product at the inlet is determined.

According to an embodiment, the temperature of the second temperature data is logged as a temperature of the food product at the outlet.

According to an embodiment, the computer system is further configured to determine whether the food product is frozen or thawed, based on the temperature of the first temperature data that is logged based on the peak current being greater than the first current threshold.

According to an embodiment, the computer system is further configured to determine wear of components of the food processing machine using weighted averages based on operating time, the current data, and at least one from among the first temperature data and the second temperature data.

According to an embodiment, the computer system is configured to use a first set of weights to obtain a weighted average corresponding to a first component, from among the components, and a second set of weights to obtain a weighted average corresponding to a second component, from among the components, the first set of weights being different from the second set of weights.

According to an embodiment, the first component is an electrical component and the second component is a mechanical component, and the second set of weights corresponding to the mechanical component, compared to the first set of weights corresponding to the electrical component, is more heavily weighted for the current data.

According to an embodiment, the computer system is further configured to: determine whether the food product is frozen or thawed, based on the temperature of the first temperature data that is logged based on the peak current being greater than the first current threshold, and determine a greater wear to one of the components based on the food product being determined to be frozen, as opposed to thawed.

According to an embodiment, the food processing machine is configured to grind meat.

According to one or more embodiments, a method performed by at least one processor is provided. The method includes: obtaining first temperature data from a first temperature sensor at an inlet of a food processing machine; obtaining second temperature data from a second temperature sensor at an outlet of the food processing machine; obtaining current data from a current sensor that is configured to measure current of a motor of the food processing machine; determining presence of food product at the inlet based on a peak current, of the current data at a time the motor starts, being greater than a first current threshold; and logging a temperature of the first temperature data based on the peak current being greater than the first current threshold.

According to an embodiment, the temperature of the first temperature data is logged as a temperature of the food product at the inlet.

According to an embodiment, the method further includes logging a temperature of the second temperature data based on a predetermined time delay after the presence of the food product at the inlet is determined.

According to an embodiment, the temperature of the second temperature data is logged as a temperature of the food product at the outlet.

According to an embodiment, the method further includes determining whether the food product is frozen or thawed, based on the temperature of the first temperature data that is logged based on the peak current being greater than the first current threshold.

According to an embodiment, the method further includes determining wear of components of the food processing machine using weighted averages based on operating time, the current data, and at least one from among the first temperature data and the second temperature data.

According to an embodiment, the determining the wear of the components includes using a first set of weights to obtain a weighted average corresponding to a first component, from among the components, and a second set of weights to obtain a weighted average corresponding to a second component, from among the components, the first set of weights being different from the second set of weights.

According to an embodiment, the first component is an electrical component and the second component is a mechanical component, and the second set of weights corresponding to the mechanical component, compared to the first set of weights corresponding to the electrical component, is more heavily weighted for the current data.

According to an embodiment, the determining the wear of the components includes: determining whether the food product is frozen or thawed, based on the temperature of the first temperature data that is logged based on the peak current being greater than the first current threshold, and determining a greater wear to one of the components based on the food product being determined to be frozen, as opposed to thawed.

According to one or more embodiments, a non-transitory computer-readable medium storing computer code is provided. The computer code is configured to, when executed by at least one processor, cause the at least one processor to: obtain first temperature data from a first temperature sensor at an inlet of a food processing machine; obtain second temperature data from a second temperature sensor at an outlet of the food processing machine; obtain current data from a current sensor that is configured to measure current of a motor of the food processing machine; determine presence of food product at the inlet based on a peak current, of the current data at a time the motor starts, being greater than a first current threshold; and log a temperature of the first temperature data based on the peak current being greater than the first current threshold.

BRIEF DESCRIPTION OF THE DRAWINGS

The above and other aspects of the present invention will become more apparent from the following description of example embodiments, taken in conjunction with the accompanying drawings of which

FIG. 6 illustrates a table of aggregated data that a computer system, according to example embodiments, may obtain.

DETAILED DESCRIPTION

The following detailed description is provided to assist the reader in gaining a comprehensive understanding of the methods, apparatuses and/or systems of the present disclosure. Various changes, modifications, and equivalents of the systems, apparatuses and/or methods described herein will suggest themselves to those of ordinary skill in the art. Descriptions of well-known functions and structures are omitted to enhance clarity and conciseness.

The terms used in the description are intended to describe embodiments only, and shall by no means be restrictive. Unless clearly used otherwise, expressions in a singular form include a meaning of a plural form. In the present description, an expression such as "comprising" or "including" is intended to designate a characteristic, a number, a step, an operation, an element, a part or combinations thereof, and shall not be construed to preclude any presence or possibility of one or more other characteristics, numbers, steps, operations, elements, parts or combinations thereof.

Figure 1:
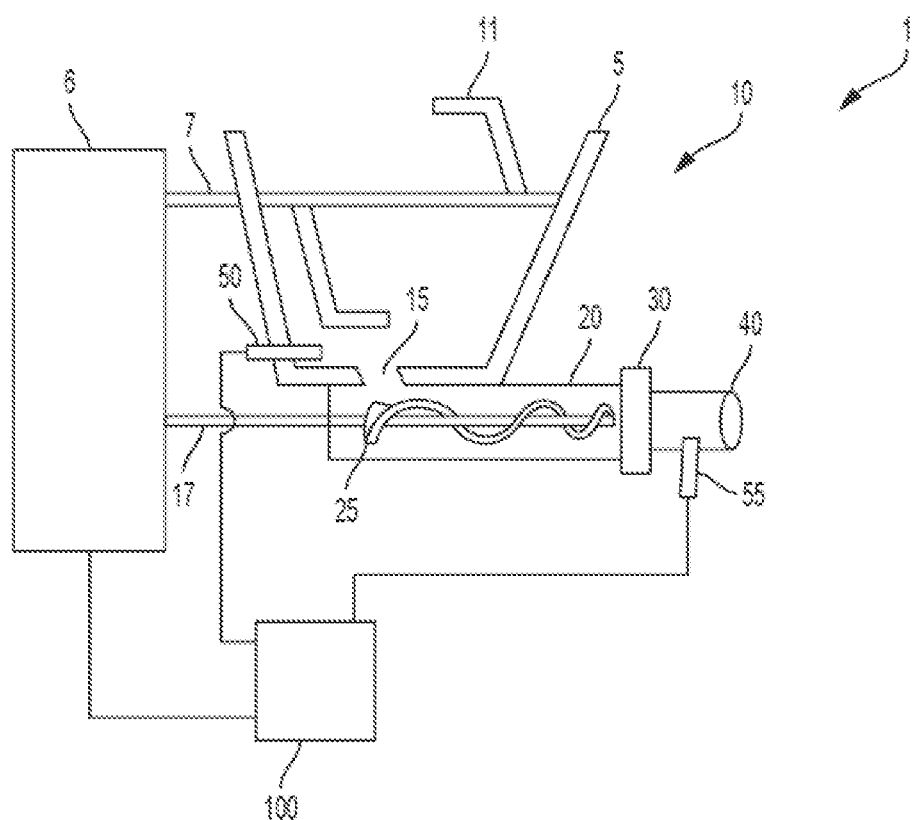
FIG. 1 illustrates a food processing monitoring system according to an example embodiment.

As illustrated in FIG. 1, in embodiments of the present disclosure, a food processing monitoring system 1 may comprise a food processing machine 10 (e.g. a meat grinder) and a data logging apparatus, such as a computer system 100 configured to collect data pertinent to product temperature at an input (e.g. a hopper 5) of the food processing machine 10 and an output (e.g. an outlet 40) of the food processing machine 10. Further, the computer system 100 may be configured to collect data (e.g. current) pertinent to motor draw of a motor 6 of the food processing machine 10. For example, the computer system 100 may communicate with a temperature sensor 50, a temperature sensor 55, and a current sensor 70 (generally designated at motor 6 in FIG. 1 and illustrated in FIG. 2) to obtain temperature data of the hopper 5, temperature data of the outlet 40, and current data of the motor 6, respectively. For example, the computer system 100 may be connected to the temperature sensor 50, the temperature sensor 55, and the current sensor 70 via one or more wires or a wireless connection.

According to an embodiment, the temperature sensor 50 and the temperature sensor 55 may be any type of sensor that is configured to sense temperature (e.g. a thermocouple). The temperature sensor 50 may be installed in a housing of the hopper 5 and the temperature sensor 55 may be installed in a housing of the outlet 40. According to an embodiment, the current sensor 70 may be any type of sensor that is configured to sense current (e.g. an ammeter). The current sensor may be installed in a housing of the motor 6 and may be electrically connected to the motor 6 to detect a load of the motor 6.

The hopper 5 may be provided with a set of mixing blades 11 that rotate. The motor 6 may be connected to a mixer shaft 7 to drive the mixing blades 11, so that a product (e.g. meat) can be mixed by tumbling the product in the hopper 5. In the bottom of the hopper 5, there is provided an opening 15 through which the mixed product can pass. Positioned beneath the opening 15 from the hopper 5 there is provided a grinding chamber 20 where a feed screw 25 leading to a grinding head 30 is located. The motor 6 is also connected to a grinder shaft 17. Grinding can be commenced by initiating driving of the feed screw 25 by the motor 6. The motor 6 can comprise two separate driving devices to drive the mixer shaft 7 and the grinder shaft 17, or may be configured so that a single driving device powers an output shaft and the output is then split between the mixer shaft 7 and the grinder shaft 17. The feed screw 25, which has may have a large pitch adjacent the opening 15 and a progressively smaller pitch toward the grinding head 30, forces the mixed product through the grinding head 30. The product exiting through an outlet 40 of the grinding chamber 20 may be a ground product such as ground meat.

Figure 2:
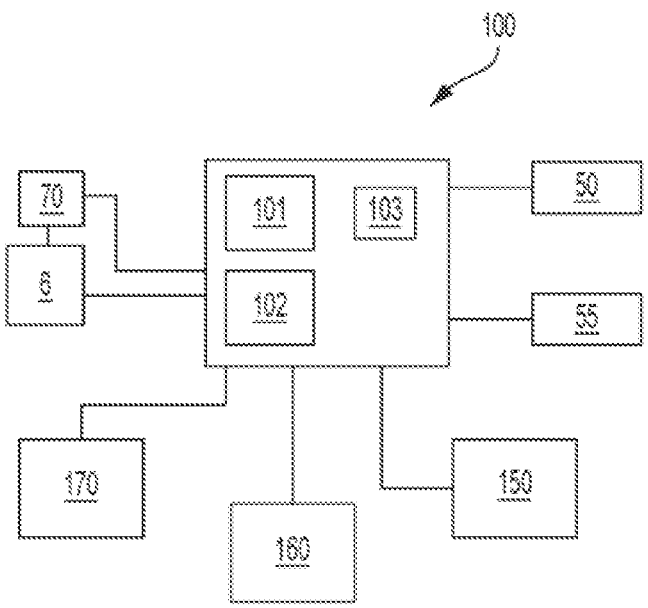
FIG. 2 illustrates a data logging apparatus according to an example embodiment.

As shown in FIG. 2, the computer system 100 may comprise at least one processor 101, a memory 102, and a transmission module 103. The transmission module 103 may comprise a wireless transmitter and receiver which communicates with external sensors and other components. In the case of wired connections, the transmission module 103 may comprise input and output ports. In FIG. 2, elements are shown schematically connected with communication lines, however such communications lines are not required to necessarily be wired connections and could, for example, be wireless.

The temperature sensor 50, the temperature sensor 55, and the current sensor 70 may provide measurement data, for example, temperature information and/or current data, to at least one processor 101 of the computer system 100. The computer system 100 is, for example, an electronic control unit which receives transmitted data, stores the data, and may control operations of the food processing machine 10. The computer system 100 may comprise integrally or separately a display 150, an input device 160, and a battery backup 170. An operator can control the machine speed and other operational parameters by manipulating the input device 160.

Figure 3:
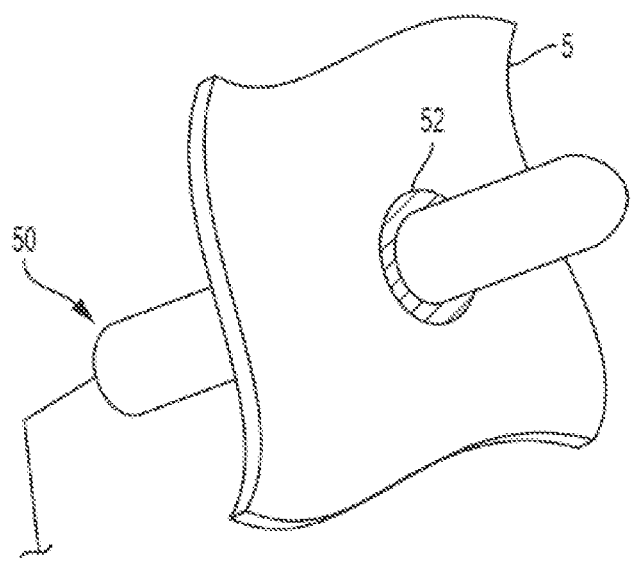
FIG. 3 illustrates a temperature sensor probe of an example embodiment.

The temperature sensor 50 and the temperature sensor 55 may be formed as probes extending through the housings and protruding into the interior of the respective chambers, wherein a seal member is interposed between the housing and the probe thereby forming a water-tight seal. For example, as illustrated in FIG. 3, the temperature sensor 50 may be a probe that extends through a housing of the hopper 5, and a seal member 52 may be interposed between the housing and the temperature sensor 50 thereby forming a water-tight seal. Alternatively, the temperature sensor 50 and the temperature sensor 55 may measure the temperature at the housing where they are installed, without protruding there through.

Figure 4:
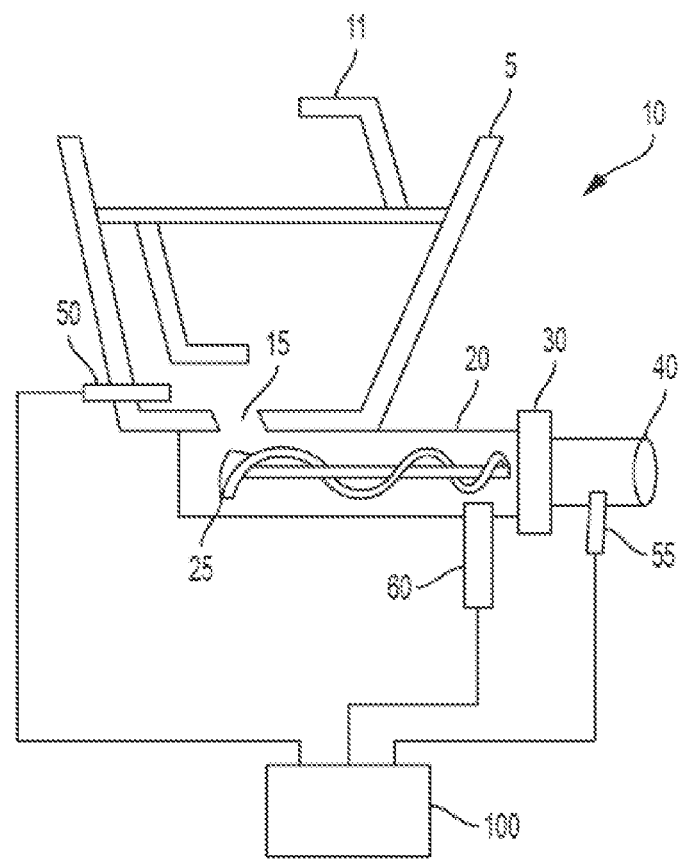
FIG. 4 illustrates another mixer grinder monitoring system according to an example embodiment.

As shown in FIG. 4, a temperature sensor 60 may be installed upstream from the grinding head 30 of the food processing machine 10. It should be noted that the number and positions of the sensors can be varied according to the desired measurements and expected batch size. Furthermore, the temperature sensors may alternatively comprise infrared thermometers which detect thermal radiation from an object at a distance.

The U.S. Department of Agriculture (USDA) may require the collection of certain data for food safety reasons, for example Hazard Analysis Critical Control Point (HACCP) data. According to embodiments, temperature data relevant to HACCP for meat processing may be automatically collected for this purpose. For example, the number and position of temperature sensors may correspond to specific Critical Control Points (CCPs) identified in the food manufacturing process for ground meat using the food processing machine 10. Pursuant to the principles of HACCP, the computer system 100 may monitor, verify, and validate operations of the food processing machine 10 and establish a record accordingly.

According to embodiments of the present disclosure, the food processing monitoring system 1 may be configured to detect whether food is present in the food processing machine 10.

For example, the computer system 100 may use a combination of temperature information logged from one or more temperature sensors (e.g. temperature sensor 50 and temperature sensor 55) with power information (e.g. current information) from one or more current sensor (e.g. current sensor 70), connected the motor 6, to provide dynamic temperature limits. The dynamic temperature limits may be food safety temperature thresholds that the computer system 100 compares with the temperature information obtained from at least one temperature sensor only when food product is determined to be present at a location (e.g. the hopper 5 or the outlet 40) corresponding to the at least one temperature sensor. According to embodiments, the at least one processor 101 of the computer system 100 may compare the detected motor power draw (e.g. current) to predetermined thresholds such as, for example, current thresholds in which values below indicate that the food processing machine 10 is operating without product present and values above indicate the food processing machine 10 is operating with various types of food product present. By using this power measurement along with the logged temperature data, the computer system 100 may determine when product is present and apply appropriate temperature thresholds at the appropriate times.

Figure 5:
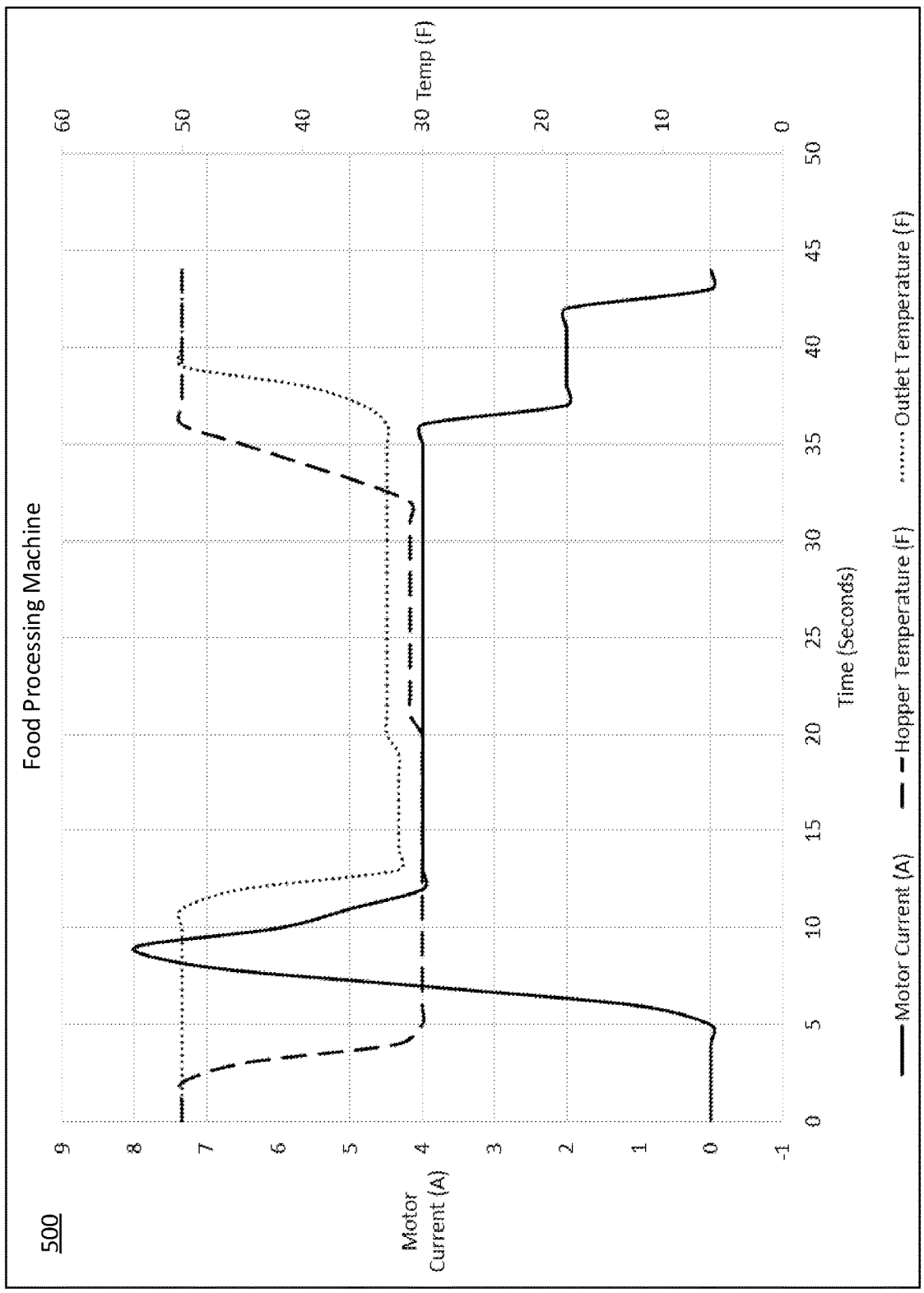
FIG. 5 illustrate a graph of example temperatures and motor current of a food processing machine, according to an example embodiment.

FIG. 5 illustrates a graph 500 that illustrates example temperatures and motor currents of the food processing machine 10 that are obtained by the computer system 100 using various temperature and current sensors according to embodiments. More particularly, FIG. 5 illustrates a temperature reading (labeled as "Hopper Temperature") of the hopper 5 and a temperature reading (labeled at "Outlet Temperature") of the outlet 40 of the food processing machine 10, along with a current draw reading (labeled as "Motor Current") from the motor 6.

The graph 500 describes an example scenario in which an operator first loads meat into the hopper 5, turns the equipment on, then allows the food processing machine 10 (e.g. a grinder) to completely process the meat before turning the food processing machine 10 off. With reference to FIG. 5, the time at "0" seconds refers to a time in which the food processing machine 10 is off and the operator first loads meat into the hopper 5.

As can be seen in FIG. 5, the temperature of the hopper 5 and the outlet 40 start at 50° F. which, in this example, is the ambient temperature in the room. At around "5" seconds, the temperature of the hopper 5 drops to 33° F. which is the starting temperature of the food product once the product is loaded into the hopper 5. When the motor 6 is first turned on at around "5" seconds, the current draw of the motor 6 rises to an initial peak of 8A at around "8" seconds, then falls to a nominal grinding current draw of 4A at around "13" seconds. At around "11" seconds, the outlet temperature starts to fall as the food product reaches the end of the outlet 40 through the food processing machine 10. After operating for a period of time, the hopper 5 is emptied due to the operation of food processing machine 10, thereby resulting in a rise in hopper temperature starting at around "32" seconds. Once the food product has been fully processed (at around "36" seconds, the motor current falls to a nominal 2A as the resistance on the motor is reduced. The outlet temperature also begins to rise at this point as there is no longer any food product present at the outlet 40.

The peak current may occur even if the hopper 5 is empty as the starting current of a motor is often larger than the nominal operating current. However, the peak current value may be higher when product is already present in the hopper 5 as opposed to when the motor 6 starts with the hopper 5 empty. According to embodiments, at an operation start time of the motor 6, the at least one processor 101 of the computer system 100 may obtain the peak current based on the current information from the current sensor 70, determine whether the peak current is above a threshold that corresponds to a current which indicates that the hopper 5 was already loaded with product before the motor 6 was started, and based on determining that the peak current is above the threshold, logging the temperature of the hopper 5, measured at the time of starting the motor 6, as the starting temperature of the food product. Alternatively, in a case where the peak current is determined to be lower than the threshold, the at least one processor 101 may determine that the hopper 5 was empty when the motor 6 was started, and log that no product was present in the hopper 5 at such time.

In a similar manner, the at least one processor 101 of the computer system 100 may determine whether product is present at the outlet 40 of the food processing machine 10 based on the current draw of the motor. However because the product requires a certain amount of time to reach the outlet 40 through the food processing machine, the at least one processor 101 may use a time delay to dynamically adjust when the temperature limits are applied. Referring to FIG. 5, it can be seen that even though product was already loaded into the equipment before the motor 6 was started, the temperature at the outlet 40 did not drop below the ambient room temperature until roughly 5 seconds after the motor 6 had been turned on. According to embodiments, the at least one processor 101 of the computer system 100 may determine a starting point at which product is determined to be in the hopper 5 with the motor running That is, for example, the at least one processor 101 may determine the starting point is a time in which the motor 6 was first turned on due to a detected starting current condition (e.g. a peak current above a threshold current) of the motor 6, or is a particular time after starting the motor 6 in which the motor current increases from a nominal current to a known grinding current. According to embodiments, the known grinding current may be a threshold current that the at least one processor 101 compares to a detected current of the motor 6 to determine whether the product is present in the hopper 5. The at least one processor 101 may determine a time in which the product is present at the outlet 40 based on a predetermined time delay from the point in time in which the product is first determined to be present at the hopper 5. For example, the processor may determine the time delay based on the length of the feed screw 25 and the outlet 40.

According to embodiments, the at least one processor 101 may continue to measure the motor current draw based on the current sensor 70 while the food processing machine 10 is operating and, based on determining that the measured motor current draw falls (e.g. below a predetermined threshold corresponding to the food fully being processed), the processor may cause a data buffer of the computer system 100 to retroactively remove food safety temperature limits based on the known period of time required for product to reach the end of the outlet 40 from the hopper 5. Alternatively or additionally, the at least one processor 101 may disable the food safety temperature limits at the outlet 40 at the point in time at which the measured motor power draw of the motor 6 drops below a predetermined current threshold indicating that grinding of food product is not occurring, which the at least one processor 101 may determine as meaning food product is no longer present.

According to embodiments, processor 101 may set the power draw thresholds and timing determinations differently based on different sizes and types of equipment, and the values used may be different depending on the type of equipment.

According to embodiments, the at least one processor 101 of the computer system 100 may perform wear rate determinations concerning the food processing machine 10. For example, by performing data collection concerning operation of the food processing machine 10, the at least one processor 101 may determine wear rate of components within the food processing machine 10, and use such wear rates to predict when maintenance should be done on a component of the food processing machine 10. According to embodiments, the at least one processor 101 may determine the wear rates based on operating time of the food processing machine 10, and also measured current draw and measured temperatures such as the motor current draw and inlet and outlet temperatures described in the present disclosure. The amount of motor current drawn correlates to mechanical resistance of the grinding medium (including whether a food product is present), and inlet or outlet temperature, when measured to be below freezing, is indicative of a solid frozen product in the food processing machine 10 as opposed to a thawed product. For example, when a grinder is operating empty for one hour, the mechanical wear on the grinder may be significantly less than when it is grinding food product. Additionally, the grinding of thawed food product (above 32° F.) may result in less mechanical wear on a system than when it is grinding frozen food product (below 32° F.). To account for this, the computer system 100 may use a weighted average approach for component wear rates and adjust the weighting based on component type. For example, electrical components such as a power supply or set of relays of a food processing machine may have an increased wear rate based solely on temperature, whereas wear rate of a set of bearings or grinding plate may be more based on the amount of time spent grinding thawed product, frozen product, and the amount of time spend rotating with no product present.

According to embodiments, the at least one processor 101 of the computer system 100 may determine wear rates of individual components (e.g. electrical components and mechanical components) by calculating, for each individual components, a weighted average by applying a set of respective weights to parameters. The parameters may include, for example, a total time in which a food processing machine (e.g. the motor) grinds food product that is frozen, a total time in which a food processing machine (e.g. the motor) grinds food product that is thawed, a total time in which a food processing machine (e.g. the motor) operates without grinding food product, and a time at one or more specified temperatures. The at least one processor 101 may set the weights for each of the parameters for an individual component based on the type of the individual component.

The at least one processor 101 may determine the value of the parameters (before the weights are applied) based on the temperature and current information that is obtained by the at least one processor 101, as described in embodiments of the present disclosure. For example, the at least one processor 101 may determine that food product is present (or not present) in the food processing machine 10 while the food processing machine 10 is operating, based on current values obtained from the current sensor 70, and further obtain temperatures of the food processing machine 10 and temperatures of the food product that is determined to be present (and therefore a frozen or thawed state of the food product) based on temperature values obtained from the temperature sensors including, for example, the temperature sensor 50 and the temperature sensor 55.

The at least one processor 101 may obtain a wear rate of each component by obtaining a weighted average for each of the components using their respective weights and parameters, and predict when maintenance should be done on a component of the food processing machine 10 based on the obtained wear rates.

According to embodiments, the at least one processor 101 of the computer system 100 may analyze the obtained temperature information and current information locally to identify and aggregate data on operation modes (e.g. grinding, operating while empty, operating above temperature limits) and report the data at the end of an operation (e.g. operation of the food processing machine 10) to limit the amount of data transfer in situations where data costs may be excessive. According to embodiments, the at least one processor 101 of the computer system 100 may aggregate data as summarized in table 600, illustrated in FIG. 6. With reference to table 600, values for "duration", "peak motor current", "average motor current", "product present", "product temperature (hopper)", "product temperature (outlet)", and "ambient temperature", and the corresponding operation modes in which the values belong, may be determined based on the obtained temperature information and/or current information from sensors. In further reference to table 600, an "x" is illustrated to indicate that a value is aggregated, and no "x" may indicate that no value is aggregated.

According to embodiments, a food processing monitoring system that includes a food processing machine that was operating for one hour may report a very small amount of data. In contrast, in a comparative embodiment, a system that uses a remote location for data analysis may require sensor readings to be transmitted once per second, requiring a significantly higher amount of data to be sent over a network.

According to embodiments, based on determining that food product is present in the food processing machine 10 and determining that a measured temperature of the food product in the food processing machine 10 is approaching an unsafe level for health (e.g. above a predetermined threshold), the at least one processor 101 of the computer system 100 may control the food processing machine 10 to prevent the temperature of the food product from exceeding the unsafe level for health. For example, the at least one processor 101 may control the feed rate of the feed screw 25 to decrease, by slowing a speed of the motor 6, based on determining that the measured temperature of the food product present at the outlet 40 rises above 38° F. By reducing the speed of the motor 6, the amount of temperature rise of the food product may be reduced. Alternatively or additionally, the at least one processor 101 may activate active temperatures controls. For example, the at least one processor 101 may cause a supply of chilled $CO_2$, from a $CO_2$ gas feed to the hopper 5 or the feed screw 25 of the food processing machine 10, to be supplied to decrease temperature of the food product. According to embodiments, the supply of the gas feed may be adjusted automatically based on the measured temperature of the food product.

Figure 7:
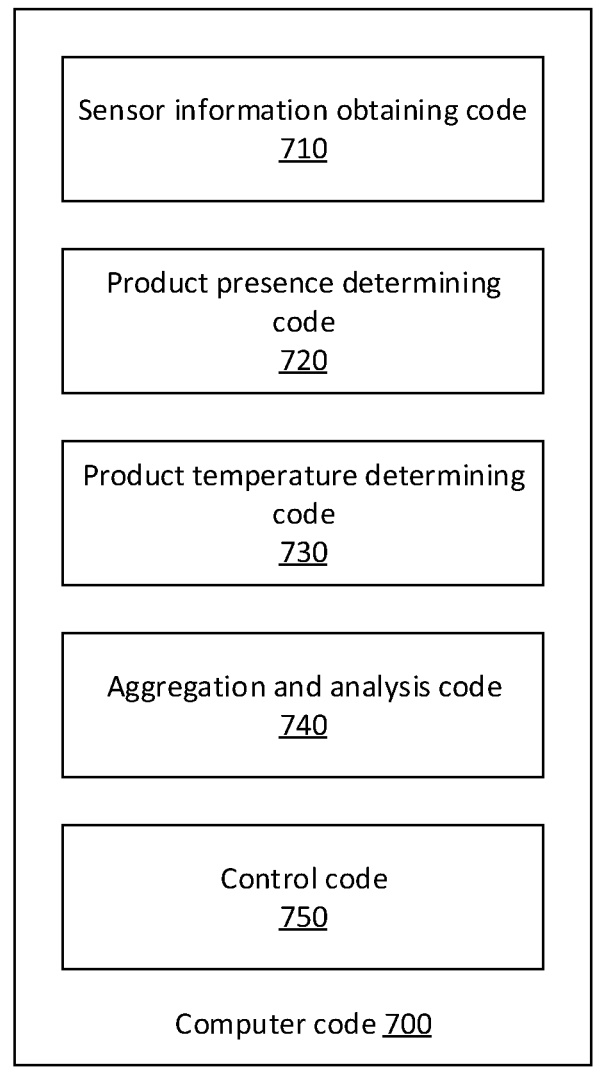
FIG. 7 is a block diagram of example code according to example embodiments.

FIG. 7 illustrates an example of computer code 700 that may be stored the memory 102 of the computer system 100. The computer code 700, when executed by the at least one processor 101, may be configured to cause the at least one processor 101 to perform its functions as described in the present disclosure. For example, the computer code 700 may comprise sensor information obtaining code 710, product presence determining code 720, product temperature determining code 730, aggregation and analysis code 740, and control code 750.

The sensor information obtaining code 710 may be configured to cause the at least one processor 101 to obtain information (e.g. temperature information and/or current information) from sensors (e.g. the temperature sensor 50, the temperature sensor 55, and/or the current sensor 70), as described with respect to embodiments the present disclosure.

The product presence determining code 720 may be configured to cause the at least one processor 101 to determine when product is present in the food processing machine 10 (e.g. at the hopper 5 and/or the outlet 40), and for how long, based on the current information and predetermined thresholds, as described with respect to embodiments of the present disclosure.

The product temperature determining code 730 may be configured to cause the at least one processor 101 to determine the temperature of product, based on determining that the product is present in the food processing machine 10 and based on the temperature information obtained while the product is present, as described with respect to embodiments of the present disclosure. The product temperature determining code 730 may also be configured to cause the at least one processor 101 to determine whether the temperature of the product is at or approaching unsafe levels by comparing the obtained product temperatures with predetermined thresholds. The product temperature determining code 730 may also be configured to cause the at least one processor 101 to determine whether the product is frozen or thawed based on the obtained temperature information.

The aggregation and analysis code 740 may be configured to cause the at least one processor 101 to aggregate and analyze the data obtained by the computer system 100, as described with respect to embodiments of the present disclosure. The analysis may include, for example, determining wear rate of components within the food processing machine 10, and using such wear rates to predict when maintenance should be done on a component of the food processing machine 10.

The control code 750 may be configured to cause the at least one processor 101 to control the food processing machine 10 to prevent the temperature of the food product from exceeding the unsafe level for health, as described with respect to embodiments of the present disclosure. For example, the at least one processor 101 may control the feed rate of the feed screw 25 to decrease, by slowing a speed of the motor 6, based on determining that the measured temperature of the food product present at the outlet 40 rises above 38° F. Alternatively or additionally, the at least one processor 101 may cause a supply of chilled CO2, from a CO2 gas feed to the hopper 5 or the feed screw 25 of the food processing machine 10.

According to embodiments, the at least one processor 101 may perform any number of the following.

The at least one processor 101 may determine temperature of food product based on temperature sensors at an inlet and outlet of a food processing machine and motor draw of a motor of the food processing machine and determine whether temperature of food product is at an unsafe level based on the measured temperatures. The at least one processor 101 may measure inlet (e.g. a hopper) and outlet temperature of a food processing machine (e.g. a grinder for meat) using respective temperature sensors; measure motor draw (e.g. current) of a motor of the food processing machine with a sensor (e.g. a current sensor); determine whether the food processing machine is operating with or without food product present by comparing the measured motor draw of the motor with at least one predetermined threshold that indicates food is being grinded (e.g. a first predetermined threshold at start of motor operation and/or a second predetermined threshold while the motor is continuously operating); log temperature of the inlet when the motor starts as temperature of food product in a case where peak measured motor draw at motor start is above the first predetermined threshold (which indicates food is within the inlet at motor start); logging that no food was present in inlet at motor start if peak measured motor draw at motor start is below or equal to first predetermined threshold (which indicates food product is not within inlet at motor start); determine that food product is presently within the inlet in a case where measured motor draw while motor is continuously running is above second predetermined threshold (and possibly logging temperature of inlet as temperature of food product based on such case); log temperature of the outlet as temperature of food product after processing based on a time delay (e.g. 5 seconds) after food product is first detected to be at the inlet; determine that processing of food product is complete (e.g. food product is not at the inlet and the outlet) based on measured motor draw dropping below a third predetermined threshold after it is determined that food product was previously at the inlet; compare temperatures of the inlet and the outlet, that are determined to correspond temperature of food product, with temperature thresholds to determine whether food is at a safe temperature (e.g. below a temperature which causes bacteria to grow); not comparing temperatures of the inlet and/or the outlet with the temperature thresholds when it is determined that food is not at the inlet and/or the outlet based on the measured voltage draw; and/or indicate (e.g. with an alarm) when food product is determined to be at an unsafe temperature.

The at least one processor 101 may determine wear rates of components of the food processing machine based on various weighted averages that are based on operating time, motor current draw, and temperature that are measured. The at least one processor 101 may determine wear rate of components of the food processing machine, and predict when maintenance on the components of the food processing machine should be performed, based on operating time, motor current draw, and temperature (e.g. at the inlet and/or the outlet). The at least one processor 101 may determine greater wear when motor current draw is a level that indicates that there is mechanical resistance of a grinding medium (i.e. grinding is occurring), and less wear when no grinding is occurring; determine greater wear when a temperature measurement(s) indicates that food product is frozen, and lesser wear when a temperature measurement(s) indicates food product is thawed; using weighted averages based on operating time, motor current draw, and temperature to determine wear of the various components (e.g. electrical components such as power supply and relays, and mechanical components such as bearing and grinding plate) of the food processing machine, wherein different weights are set for operating time, motor current draw, and temperature based on types of components for determining component wear rate (e.g. electrical component may solely use temperature for determining component wear rate, while mechanical components may use weights of each characteristic to different degrees).

The at least one processor 101 may perform analysis locally and report data over internet after a process is complete. The analysis may identify operational modes (e.g. startup, operating without product, grinding, grinding complete) and applicable data concerning operational modes (e.g. duration of mode, peak motor current during mode, average motor current during mode, whether food product is present during mode, food product temperature at the inlet during mode, food product temperature at outlet during mode, ambient temperature during mode) may be aggregated. The at least one processor 101 may report data from the analysis over a network (e.g. the internet) after completion of an operation (e.g. grinding complete).

The at least one processor 101 may control a motor or add chilled CO2 based on inlet and outlet temperature. For example, the at least one processor 101 may control a feed rate of a screw drive of the food processing machine or an amount of chilled CO2 introduced via a gas feed into the food processing machine based on inlet (e.g. hopper) or screw temperature to avoid the temperature of the food product that is measured at the outlet rising above a predetermined temperature (e.g. 38 degrees F.).

It should be noted that although a few non-limiting example embodiments have been described, those skilled in the art will readily appreciate that many modifications are possible to the example embodiments without departing from the scope of the present disclosure. Therefore, it is to be understood that the foregoing is illustrative of various example embodiments and is not to be construed as limited to the specific example embodiments described herein.

What is claimed is:

1. A food processing monitoring system comprising:
   a food processing machine comprising:
      an inlet configured to receive food product;
      an outlet configured to receive the food product after being processed;
      a processing chamber that is connected to the inlet and the outlet;
      a rotatable shaft that is within the processing chamber; and
      a motor that is configured to rotate the rotatable shaft such as to cause the food product to be processed in the processing chamber;
   a first temperature sensor provided at the inlet;
   a second temperature sensor provided at the outlet;
   a current sensor configured to measure current of the motor; and
   a computer system comprising memory and at least one processor, the computer system configured to:
      obtain first temperature data from the first temperature sensor;
      obtain second temperature data from the second temperature sensor;
      obtain current data from the current sensor;
      determine presence of the food product at the inlet based on a peak current, of the current data at a time the motor starts, being greater than a first current threshold;
      log a temperature of the first temperature data based on the peak current being greater than the first current threshold; and
      determine wear of components of the food processing machine using weighted averages based on operating time, the current data, and at least one from among the first temperature data and the second temperature data.

2. The food processing monitoring system of claim 1, wherein the temperature of the first temperature data is logged as a temperature of the food product at the inlet.

3. The food processing monitoring system of claim 1, wherein the computer system is further configured to log a temperature of the second temperature data based on a predetermined time delay after the presence of the food product at the inlet is determined.

4. The food processing monitoring system of claim 3, wherein the temperature of the second temperature data is logged as a temperature of the food product at the outlet.

5. The food processing monitoring system of claim 1, wherein the computer system is further configured to determine whether the food product is frozen or thawed, based on the temperature of the first temperature data that is logged based on the peak current being greater than the first current threshold.

6. The food processing monitoring system of claim 1, wherein the computer system is configured to use a first set of weights to obtain a weighted average corresponding to a first component, from among the components, and a second set of weights to obtain a weighted average corresponding to a second component, from among the components, the first set of weights being different from the second set of weights.

7. The food processing monitoring system of claim 6, wherein
   the first component is an electrical component and the second component is a mechanical component, and
   the second set of weights corresponding to the mechanical component, compared to the first set of weights corresponding to the electrical component, is more heavily weighted for the current data.

8. The food processing monitoring system of claim 1, wherein the computer system is further configured to:
   determine whether the food product is frozen or thawed, based on the temperature of the first temperature data that is logged based on the peak current being greater than the first current threshold, and
   determine a greater wear to one of the components based on the food product being determined to be frozen, as opposed to thawed.

9. The food processing monitoring system of claim 1, wherein the food processing machine is configured to grind meat.

10. A method performed by at least one processor, the method comprising:
    obtaining first temperature data from a first temperature sensor at an inlet of a food processing machine;
    obtaining second temperature data from a second temperature sensor at an outlet of the food processing machine;
    obtaining current data from a current sensor that is configured to measure current of a motor of the food processing machine;
    determining presence of food product at the inlet based on a peak current, of the current data at a time the motor starts, being greater than a first current threshold;
    logging a temperature of the first temperature data based on the peak current being greater than the first current threshold;
    controlling operation of the food processing machine based on the temperature of the first temperature data; and
    determining wear of components of the food processing machine using weighted averages based on operating time, the current data, and at least one from among the first temperature data and the second temperature data.

11. The method of claim 10, wherein the temperature of the first temperature data is logged as a temperature of the food product at the inlet.

12. The method of claim 10, further comprising logging a temperature of the second temperature data based on a predetermined time delay after the presence of the food product at the inlet is determined.

13. The method of claim 12, wherein the temperature of the second temperature data is logged as a temperature of the food product at the outlet.

14. The method of claim 10, further comprising determining whether the food product is frozen or thawed, based on the temperature of the first temperature data that is logged based on the peak current being greater than the first current threshold.

15. The method of claim 10, wherein the determining the wear of the components of the food processing machine using weighted averages comprises using a first set of weights to obtain a weighted average corresponding to a first component, from among the components, and a second set of weights to obtain a weighted average corresponding to a second component, from among the components, the first set of weights being different from the second set of weights.

16. The method of claim 15, wherein
the first component is an electrical component and the second component is a mechanical component, and
the second set of weights corresponding to the mechanical component, compared to the first set of weights corresponding to the electrical component, is more heavily weighted for the current data.

17. The method of claim 10, wherein the determining the wear of the components comprises:
determining whether the food product is frozen or thawed, based on the temperature of the first temperature data that is logged based on the peak current being greater than the first current threshold, and
determining a greater wear to one of the components based on the food product being determined to be frozen, as opposed to thawed.

18. A non-transitory computer-readable medium storing computer code that is configured to, when executed by at least one processor, cause the at least one processor to:
obtain first temperature data from a first temperature sensor at an inlet of a food processing machine;
obtain second temperature data from a second temperature sensor at an outlet of the food processing machine;
obtain current data from a current sensor that is configured to measure current of a motor of the food processing machine;
determine presence of food product at the inlet based on a peak current, of the current data at a time the motor starts, being greater than a first current threshold;
log a temperature of the first temperature data based on the peak current being greater than the first current threshold;
control operation of the food processing machine based on the temperature of the first temperature data; and
determine wear of components of the food processing machine using weighted averages based on operating time, the current data, and at least one from among the first temperature data and the second temperature data.

\* \* \* \* \*